United States Patent
Giuliano et al.

(10) Patent No.: US 7,378,081 B2
(45) Date of Patent: May 27, 2008

(54) COMPOSITION AND METHOD FOR DIRECT VISUALIZATION OF THE HUMAN APPENDIX

(75) Inventors: Vincenzo Giuliano, Winter Springs, FL (US); Concetta Giuliano, Winter Springs, FL (US)

(73) Assignee: Vincon Research Enterprises, LLC, Winter Springs, FL (US)

( * ) Notice: Subject to any disclaimer, the term of this patent is extended or adjusted under 35 U.S.C. 154(b) by 0 days.

(21) Appl. No.: 11/484,296

(22) Filed: Jul. 11, 2006

(65) Prior Publication Data

US 2006/0251577 A1 Nov. 9, 2006

Related U.S. Application Data

(63) Continuation-in-part of application No. 11/104,700, filed on Apr. 13, 2005, which is a continuation-in-part of application No. 10/354,644, filed on Jan. 29, 2003, now abandoned.

(51) Int. Cl.
*A61K 49/04* (2006.01)
(52) U.S. Cl. ...................... 424/9.45; 424/9.4
(58) Field of Classification Search ............ 424/9.45, 424/9.4
See application file for complete search history.

(56) References Cited

U.S. PATENT DOCUMENTS

| | | | |
|---|---|---|---|
| 4,192,859 A | 3/1980 | Mackaness | |
| 4,474,747 A | 10/1984 | Dimo et al. | |
| 4,735,795 A | 4/1988 | Robinson et al. | |
| 5,233,995 A | 8/1993 | Yudelson et al. | |
| 5,242,683 A * | 9/1993 | Klaveness | 424/9.35 |
| 5,360,604 A | 11/1994 | Ruddy et al. | |
| 5,599,577 A * | 2/1997 | Stevens et al. | 427/2.14 |
| 5,716,642 A | 2/1998 | Bagchi et al. | |
| 5,770,181 A * | 6/1998 | Kirkland | 429/9.37 |
| 6,375,931 B2 | 4/2002 | Ostensen et al. | |
| 6,409,671 B1 | 6/2002 | Eriksen et al. | |
| 6,424,857 B1 | 7/2002 | Henrichs | |
| 6,426,077 B1 | 7/2002 | Grace et al. | |
| 2004/0241093 A1* | 12/2004 | Lauenstein et al. | 424/9.3 |
| 2005/0180921 A1 | 8/2005 | Taylor et al. | |

OTHER PUBLICATIONS

Giuliano et al. (Emer. Radiol. 2004, 10, 235-237).*

* cited by examiner

*Primary Examiner*—Michael G. Hartley
*Assistant Examiner*—Melissa Perreira
(74) *Attorney, Agent, or Firm*—Robert Plotkin, P.C.; Edward M. Livingston, Esq.

(57) ABSTRACT

A positive contrast agent composition containing meglumine diatrizoate, sodium diatrizoate, simethicone, famotidine and aspartame in predetermined amounts that is orally administered to a patient for clinical evaluations of appendicitis wherein a positive contrast effect is achieved. Methods of use include orally administering individual doses of the composition approximately 50 minutes prior to appendix visualization using computerized axial tomography.

3 Claims, 4 Drawing Sheets

COMPOSITION AND METHOD FOR DIRECT VISUALIZATION OF THE HUMAN APPENDIX

CROSS-REFERENCE TO RELATED APPLICATION

This is a continuation-in-part application of Ser. No. 11/104,700 filed Apr. 13, 2005, which was a continuation-in-part application of Ser. No. 10/354,644 filed Jan. 29, 2003, now abandoned.

BACKGROUND OF THE INVENTION

This invention relates to a composition and method for direct visualization of the human appendix and method, more particularly, to a composition for use in direct visualization of the human appendix and method for diagnosing appendicitis that provides direct and unambiguous visualization of the human appendix, separate and distinct from the gastrointestinal tract.

The gastrointestinal tract is a long hollow tube, or viscus, extending from the mouth to the anus, and includes the stomach, small intestine, colon, and large intestine. The gastrointestinal tract has an important and necessary physiologic function in the digestion of food into biologically usable form to sustain life.

On the other hand, unlike the gastrointestinal tract, the appendix is not a hollow tube and does not participate in any gastrointestinal function. In fact, the appendix currently has no known biologic function. Instead, the appendix is an organ, distinct from the gastrointestinal tract and not related to digestive function, that is believed to be a vestigial structure, or remnant. In anatomic descriptions, the appendix is a blind-ending pouch, 7 to 8 cm in length, connected to the cecum. The appendix contains lymphoid tissue but it is uncertain whether this serves a physiologic role in lymphoid function.

Based on these distinct anatomic and physiologic differences, the appendix is by definition not considered part of the gastrointestinal tract. These differences make it particularly challenging to visualize and detect pathology of the appendix in humans.

Computed tomography (CT scan) is an imaging technology used to obtain detailed cross-sectional imaging of the human body tissues and organs. Small and insignificant organs, such as the appendix, are amenable to visualization and detection using CT scans. During a CT scan, a rotating x-ray machine and detector assembly rotate around the patient to produce a large number of radiographic images which are in turn stored in a computer for display and archival. Controlled amounts of radiation pass through the body and are attenuated by body tissues and organs, thereby producing radiographic images.

Typical CT examinations can be performed in only a few minutes. The patient lies supine on a table and passes through a narrow tunnel called the gantry, as a rotating x-ray machine and detector assembly capture two dimensional radiographic images of the human body. Because the scan increments can be exceedingly small, on the order of a few millimeters, CT scan can be adapted for organ-specific imaging, such as the appendix. An additional benefit of the CT scan is its speed and non-invasive technology, amenable to the testing of sick, elderly, and pediatric patients, either in a hospitalized or outpatient setting.

In preparing patients for the CT examination, radiopaque materials, also known as radiodense materials, collectively termed contrast agents, can be administered orally and/or intravenously, to produce further attenuation of the x-ray beam, creating optimal image contrast. The net effect of radiopaque contrast agents is that organ and tissue contrast appear white on the radiographic image. Body organs and tissues take up intravenous contrast agents, providing a temporary window of opportunity to study physiologic functions and detailed anatomic information. Oral contrast agents fill hollow tubes, including the esophagus, stomach, and bowel, all of which are considered part of the gastrointestinal or alimentary tract, providing additional information regarding bowel function and pathology.

The speed and accuracy of CT scans are essential in the diagnosis of potentially life threatening medical conditions, including appendicitis, an inflammatory condition of the appendix. During an appendicitis event, the orifice or opening the appendix becomes obstructed due to unknown factors, presumably hypertrophy of lymphoid tissue within the appendix. A build-up of purulent collection builds up within the appendix and can perforate freely into body cavities, resulting in sepsis, which is widespread dissemination of infection throughout the body, and potential death. Purulent concretions can also calcify to form small calculi called appendicoliths.

Thus, appendicitis is a legitimate public health concern. In fact, appendicitis has a lifetime risk of between 1 in 7 and 1 in 9 persons, and over 700,000 cases are evaluated in emergency wards in the United States each year. Delayed or missed appendicitis is among the leading causes of medical liability, which involve principally the morbidity and mortality complications associated with perforation and sepsis, which can occur rapidly, without warning, proving potentially catastrophic to the patient. The perforated appendicitis risk is approximately 65% in the pediatric population, but much less in adults, possibly 1 in 500.

Appendicitis also presents an added diagnostic dilemma, and can evade timely medical diagnosis. A significant number of patients fail to show the classic clinical signs of appendicitis, such as right lower quadrant peritoneal tenderness, fever, and leukocytosis (elevated white blood cell count). In these clinical settings, CT scans can be used to significantly reduce the risk of delayed or missed appendicitis.

One of the difficulties with appendicitis diagnosis is that appendicitis is not part of the gastrointestinal tract and has no known gastrointestinal function. Appendicitis and bowel diseases do not have a common anatomic basis, form, function, or mechanism of disease. In diseases of the bowel, the bowel can become obstructed, leading to abdominal distention and changes in bowel function, such as changes frequency or consistency of bowel movements. Appendicitis produces no such early warning signs. When appendicitis occurs, it often has progressed to the point of frank perforation or peritonitis. In the common practice of performing CT examinations, there also can be a significant time lag between the imaging findings and clinical manifestations of appendicitis.

Further compounding this diagnostic dilemma is the lack of a unified medical consensus regarding the optimal technique for CT scans of the appendix, including the optimal response time between performing a CT scan and obtaining reliable diagnostic results. In actual practice, this response time can lag by as much as 4 to 6 hours or more, an unacceptable standard. Many appendicitis patients are encountered in the outpatient setting in doctor's offices and clinics, but cannot be evaluated in the typical outpatient radiology facility because of significant time limitations and the lack of an available safe diagnostic pharmaceutical agent to facilitate rapid diagnosis.

In descriptions of the prior art, indirect methods of visualizing the appendix must be distinguished from direct methods. Added distinctions also must be made regarding the contrast agent used in the indirect method of evaluation. The choice of contrast agent can be either a positive contrast agent, which appears radiopaque, or radiodense, on the CT scan image, versus a negative contrast agent, which are not radiopaque on the CT scan image. Radiodensity generally appears white on the CT scan image; whereas absence of radiodensity appears black on the CT scan image. Body organs and tissues result in variable attenuation of the x-ray beam, producing a spectrum of image contrast, from white, to gray, to black.

Diatrizoate, a radiopaque contrast agent, is designated chemically as 1-deoxy-1-(methylamino)-D-glucitol-3,5-diacetamido-2,4,6-triiodobenzoate. Gastrografin® and Gastroview® are commercially available forms of diatrizoate, dispensed in a liquid form containing a solution of diatrizoate salts, and are typically used for visualization of the gastrointestinal tract. The potential dosing possibilities of these solutions are infinite but limited by the concentration of diatrizoate salts in solution. However, the most important characteristic of diatrizoate is the high atomic weight of iodine, which allows sufficient radiodensity for visualization of surrounding tissues.

The prescribed adult dosage is 25 mL of Gastrografin® in 1500 mL of water, producing a prepared solution containing 0.6% iodine. Barium suspension is another radiopaque contrast agent and the most commonly used for CT examinations of the gastrointestinal tract. However, barium suspension is contraindicated in clinical evaluations for appendicitis because of the risk of barium-induced peritonitis when barium suspension spills freely into the peritoneal cavity. Barium suspension cannot be used as a practicable alternative contrast media when dealing with bowel perforations or indirect evaluation of the appendix.

Examples of non-radiopaque contrast agents used for CT examinations of the gastrointestinal tract include water, methylcellulose, polyethylene glycol, hydrocolloid, and perfluorocarbons.

During a routine examination of the gastrointestinal tract, the appendix is not directly visualized as it is not part of the gastrointestinal tract. However, the appendix can form an impression or indentation on the bowel during an examination, resulting in an indirect method of visualizing the appendix, which is also known as a negative contrast effect. A positive contrast effect is one in which a radiopaque contrast agent, also known as a positive contrast agent, is concentrated directly within the organ of interest.

Gastrointestinal tract examinations in the prior art can be performed for indirect visualization of the appendix using either radiopaque (positive contrast) or non-radiopaque (negative contrast) agents. However, there are no positive contrast agents available or known commercially that produce an organ-specific positive contrast effect, i.e., concentration within the appendix. An ideal diagnostic pharmaceutical agent for diagnosis of appendicitis is one which is an organ-specific positive contrast agent (radiopaque) and which concentrates within the appendix, producing a positive contrast effect.

The use of negative contrast agents in the prior art has been well studied and lead to the same conclusion: there are significant inherent technical limitations in the evaluation of appendicitis. One of the major drawbacks of negative contrast agents is that they produce a weak bowel opacification that renders the agent useless for direct visualization of the appendix. The considerable bowel distention from air and fluid associated with negative contrast agents often obscures the appendix, which is not part of the gastrointestinal tract. Consequently, the confident diagnosis of appendicitis is rendered ambiguous and not obvious. Significant clinical side effects are also problematic and include diarrhea and patient non-compliance related to bowel distention and discomfort from excessive oral fluid intake, in addition to gaseous distention produced by the addition of mannitol, sorbitol, and sugar-based flavoring agents. The work of Megibow has further shown that a negative contrast effect is not considered sufficient clinically to allow for a confident diagnosis of appendicitis.

Megibow has investigated the extensive use of negative contrast agents available in the prior art, also encompassing those described herein, and concluded that negative contrast agents are not reliable in the diagnosis of appendicitis. Even when sufficient bowel distention has been achieved, the confident diagnosis of appendicitis is not rendered unambiguous or obvious. Particularly when the appendix is surrounded by multiple distended bowel loops, containing air and fluid, the negative contrast effect can further obscure visualization of the appendix.

One of the principal reasons that indirect methods fail to provide direct or organ-specific appendiceal visualization is that the primary goal of negative contrast agents is to visualize the bowel, not the appendix. The indirect visualization of the appendix by forming an impression or indentation on distended bowel loops appears to be an incidental or secondary result or benefit. As noted above, however, the appendix is not part of the gastrointestinal tract. Consequently, appendicitis is not a disease of the gastrointestinal tract, as diseases of the gastrointestinal tract and appendicitis do not have a common origin, causative factor, or mechanism. In order for pharmaceutical agents to work effectively in the appendix, they must target the appendix by considering the distinct and defined differences in anatomy and physiologic function between the appendix and the gastrointestinal tract.

Multiple examples of indirect methods of visualizing the appendix in the prior art reinforce the shortcomings of using gastrointestinal contrast agents to achieve a negative, rather than positive, contrast effect, regardless of whether they are negative contrast agents or positive contrast agents.

In contradistinction to indirect methods of visualizing the appendix, producing a negative contrast effect, a positive contrast agent is one in which there is organ-specific concentration of a pharmaceutical agent, producing a positive contrast effect. Therefore, positive contrast agents producing a positive contrast effect are preferable and represent an ideal pharmaceutical agent.

Neutrospect is an agent in the prior art that can produce a positive contrast effect in the appendix, but the result is not organ-specific. The mechanism of action involves the intravenous administration of radiolabelled murine myoclonal antibodies, which bind to human neutrophils in vivo. The radiolabelled antibodies are sequestered and accumulated in the peri-appendiceal area during an appendicitis event, and an imaging camera detects the radioactivity in the form of a spot on the radiographic film. However, Neutrospect is not site or organ specific for appendicitis and can be associated with any type of infection.

There are a number of inherent technical and therapeutic limitations of using Neutrospect in the clinical setting. First, it is of limited value clinically because it is not organ specific and has limited specificity. Neutospect accumulates not only in the appendix but in any target organ where there is an accumulation of neutrophils, as occurs with other infections, such as inflammatory bowel disease, diverticulitis, and intracavitary abscesses or collections. A positive Neutospect scan can produce an accumulation of radioactivity, or a spot on the radiographic film, practically anywhere in the body where there is an infection, confounding the clinician and further rendering a diagnosis of appendicitis as ambiguous and not obvious.

In addition, significant safety issues preclude the safe administration of Neutrospect in human subjects for appendicitis diagnosis. The United States Food and Drug Administration recently suspended clinical use of Neutrospect following documented incidents of fatal anaphylactic reactions leading to cardiopulmonary demise in several hospitalized patients. The long-term implications and future of Neutrospect are presently unclear. However, these significant safety issues, in addition to limited specificity for appendicitis diagnosis, preclude Neutrospect as a practicable diagnostic pharmaceutical for clinical use, particularly in the outpatient setting.

A definite need exists for an organ-specific or purpose-limited diagnostic pharmaceutical agent for appendicitis diagnosis due to the large numbers of subjects with potential lifetime risk for developing appendicitis, estimated at between 1 in 7 and 1 in 9 persons. No such ideal pharmaceutical agent is available commercially for routine clinical application.

Because of the possibilities for large numbers of patients undergoing diagnostic evaluations for appendicitis, particularly in the outpatient setting, a further need exists for a safe diagnostic pharmaceutical agent, in addition to being organ-specific or purpose-limited for appendicitis. Also not provided in the prior art is an ideal diagnostic pharmaceutical that can be easily manufactured in read-to-use packaged individual unit doses adapted for convenient and efficient outpatient usage.

Thus, a need exists for an oral composition of diatrizoate salts which provide a sufficient and faster rate for computerized axial tomographic examinations concentrating in the appendix wherein the contrast media is concentrated in the appendix.

The prior art contains contrast agents but none like the present invention, as follows:

| Patent Number | Inventor | Issue Date |
|---|---|---|
| 5,233,995 | Yudelson et al. | Aug. 10, 1993 |
| 4,735,795 | Robinson et al. | Apr. 05, 1988 |
| 5,360,604 | Ruddy et al. | Nov. 01, 1994 |
| 6,424,857 | Henrichs et al. | Jul. 23, 2002 |
| 6,375,931 | Ostensen et al. | Apr. 23, 2002 |
| 6,409,671B1 | Eriksen et al. | Jun. 25, 2002 |
| 5,716,642 | Bagchi et al. | Feb. 10, 1998 |
| 4,474,747 | Dimo et al. | Oct. 02, 1984 |
| 2004/0241093 | Lauenstein | Dec. 02, 2004 |
| 5,770,181 | Kirkland | Jun. 23, 1998 |
| 2005/0180921 | Taylor et al. | Aug. 18, 2005 |
| 6,426,077 | Grace et al. | Jul. 30, 2002 |
| 5,242,683 | Klaveness | Sep. 07, 1993 |
| 4,192,859 | Mackaness et al. | Mar. 11, 1980 |

SUMMARY OF THE INVENTION

The primary object of the present invention is to provide a composition that concentrates in the appendix to enable its direct visualization using computerized axial tomography, a medical diagnostic imaging modality.

Another object of the present invention is to provide a composition that is a positive contrast agent that produces an organ-specific positive contrast effect.

Another object of the present invention is to provide a composition which reduces the amount of oral intake required for sufficient gastrointestinal contrast.

Another object of the present invention is to provide a composition which reduces the amount of undesirable patient side effects, such as diarrhea.

A further object of the present invention is to provide such a composition which eliminates the need for preparation of oral contrast media in advance by trained medical personnel in preparation for computerized axial tomography examinations.

An even further object of the present invention is to provide a composition which is packaged for efficient, economical storage in bulk quantities.

An additional object of the present invention is to provide such a composition which is colored to aid in the identification of bowel perforation in an operative setting.

A yet even further objective of the present invention is to provide a composition which achieves an optimal range of pH and gasless enteric state the results in a particularly favorable release profile for the active enhancing agent.

The present invention fulfills the above and other objects by providing an oral crystalline composition having a combination of diatrizoate salts, simethicone and famotidine in predetermined amounts to result in rapid, direct and unambiguous visualization of the human appendix in conjunction with computerized tomography (CT scans). The composition fulfills all of the pertinent clinical criteria for an ideal practicable diagnostic pharmaceutical agent for appendicitis diagnosis as it is organ-specific, purpose-limited, safe for extensive outpatient usage and has negligible side effects. In addition, the composition is highly-effective based on a favorable bioavailability in sufficient quantity to facilitate passive diffusion and concentration within the appendix within a short enough time period for imaging and has a favorable release profile for the active enhancing agent, diatrizoate. The composition would be orally administered at a pre-determined time period prior to conducting the computerized axial tomographic examination.

The above and other objects, features and advantages of the present invention should become even more readily apparent to those skilled in the art upon a reading of the following detailed description of the preferred embodiments of the invention.

BRIEF DESCRIPTION OF THE DRAWINGS

In the following detailed description, reference will be made to the attached drawings in which.

DESCRIPTION OF THE PREFERRED EMBODIMENTS

Figure 1:
FIG. 1 is a CT scan indicating a contrast opacified appendix after administration of the composition of the present invention.

The invention is regarded as a positive contrast agent. A positive contrast agent is an internally administered substance that has a different density or opacity from tissue or organ densities seen on a computed tomography (CT) scan. A positive contrast agent is one that appears radiodense, or radiopaque, appearing as a white defect on a CT scan. A positive contrast agent must be differentiated from a positive contrast effect, a situation where a positive contrast agent is selectively concentrated in an organ of interest, such as the appendix. A positive contrast agent could also produce a negative contrast effect. For instance, the appendix could form an impression or indentation of a distended loop of bowel containing a positive contrast agent, producing a negative contrast effect in the visualization of the appendix. This is the typical method encountered in the prior art.

The composition of the present invention, is 'purpose limited,' i.e., in the first medical use format, distinguishing it from agents known in the prior art for known independent uses. For instance, there is no prior disclosure of the use of diatrizoate as organ-specific or purpose limiting for appendicitis diagnosis. Rather, it is described as a bowel contrast agent. The new medical use of diatrizoate as organ-specific in appendicitis diagnosis is therefore justified as being novel. Distinct and defined differences in anatomy and physiologic function distinguish appendicitis as not being a disease of the gastrointestinal tract. In addition, diseases of the gastrointestinal tract and appendicitis do not have a common origin, causative factor, or mechanism.

Further justification of novelty of the proposed invention is the unique mechanism of action and pharmakinetic profile of the pharmaceutical composition, supporting a particularly favorable release profile for the positive contrast agent, diatrizoate, increasing its bioavailability in sufficient quantity to facilitate passive diffusion and concentration within the appendix, within a short enough time period for imaging.

Clinical data reproduced in experimental subjects suggests that organically bound iodine contained in diatrizoate is passively delivered and concentrated in the human appendix approximately 50 minutes following oral administration. The bioavailability and release profile of diatrizoate appear dependent on both concentration and pH, which explains why uses of diatrizoate in the prior art fail to concentrate in the appendix. The composition of the present invention modifies the prior art by including additional agents, such as simethicone and famotidine, to provide the optimal pH and enteric state to preserve the bolus of diatrizoate.

Critical to efficacy of the composition are 'gasless' enteric conditions and neutralization of the harsh acidity of gastric secretions that appear to inhibit the transit of intact diatrizoate to the appendix. Clinical trials show optimal appendiceal visualization at a critical concentration of 2.8 mg % iodine; however 5 mg % is considered optimal for ideal image contrast.

In addition, the inclusion of famotidine provides a smooth muscle stimulatory effect on the appendix via histamine (H-2) receptor blockade to allow diatrizoate to passively diffuse into the appendix.

In addition, the composition of the present invention also includes aspartame based on its selection as the only appropriate sweetening agent because of its unique physiology. In the intestinal villi, aspartame is metabolized to phenylalanine and aspartic acid, producing no carbon dioxide, a typical an expected byproduct of many sweetening agents used in the prior art, such as mannitol, sucrose, and fruit juices. Sugars produce copious amounts of carbon dioxide, inhibiting and thereby precluding delivery of the intact bolus of diatrizoate to the appendix. The use of sugars is another key reason why preparations in the prior art failed to concentrate in the appendix. The use of aspartame is therefore included as a novel and necessary step in the bioavailability and delivery of intact diatrizoate to the appendix.

The composition of the present invention has been administered successfully, without incident, to 629 patients between the ages of 18 to 59 years, in a series of reproducible and well-documented clinical studies in adult patients. Excellent results also have been encountered in patients aged 4 to 18 years and greater than 60 years, but these results have not been formally documented.

In 100 patients evaluated for appendicitis using the invention, appendicitis diagnosis was achieved with a specificity of 99%, with mean visualization of the appendix of 84% at 50 min following oral administration.

Because of the unprecedented high specificity, the composition of the present invention was determined to be most effective method in excluding appendicitis, reducing false positive results. The high specificity is of great value in the clinical setting where visualization of the appendix is indicated, particularly in a clinical presentation that is ambiguous and unclear, which is often the case. Although imaging may be the only means of detecting appendicitis, the results yielded are often indeterminate or ambiguous because the appendix, a small and insignificant structure, cannot be directly visualized. This situation is very typical in adult patients, who can present with vague right lower quadrant pain on an intermittent or even chronic basis, without any of the classic clinical features of appendicitis. In fact, fever, elevated white count (leukocytosis), and peritoneal inflammation can be surprisingly absent. Often there is the mistaken assumption among clinicians that appendicitis is a fulminant and progressive medical condition, leading to eventual perforation and peritonitis, requiring immediate surgery, which is not the case in adult patients.

Consequently, larger scale clinical investigations were performed to determine whether the interpreting radiologist could visualize the appendix without ambiguity or uncertainty. Subsequent evaluations with a larger scale clinical trial of 525 patients showed improved image interpretation confidence in visualization of the appendix using said composition in conjunction with focused CT examinations of the right lower quadrant. A five-point scale was used to assess the effect of contrast enhancement of the appendix and appendiceal area on overall reader confidence. The composition of the present invention improved visualization of the normal appendix in 446 of 504 (88%) patients, with a specificity of 99%. The high specificity is particularly useful clinically in being able to reliably exclude appendicitis, and represents the most significant advantage over the prior art.

A small clinical trial, a pilot study comprising four adult patients using said composition, identified chronic appendicitis 'syndrome,' a newly described clinical entity manifested by appendicolithiasis with thickened appendix, as a rare cause of chronic right lower quadrant pain in adults. The study also showed that the said composition was safe and effective in patients with documented, that is, surgically proven, perforated appendicitis.

Reproducible experimental supports the novel new use of diatrizoate and other ingredients in said composition for direct visualization of the human appendix in clinical CT examinations. While it is recognized that diatrizoate could be used in the prior art to visualize bowel and produce a possible negative contrast effect in order to visualize the appendix, these properties are not of clinical value, as reinforced by Megibow.

Said composition also involves the combination of known independent agents, which is novel and not obvious from the prior art. The second medical use of diatrizoate for use in direct imaging of the appendix achieves a different end-result from the prior art, rather than merely a different method of obtaining the end-result. There are distinct differences between said composition compared to known clinical uses of diatrizoate as a diagnostic imaging agent in the prior art.

First, said composition is adapted in a form, a powdered formulation, which is novel and inventive, compared to a liquid used in the prior art. The powder form resulted in a particularly favorable release profile for the active agent, diatrizoate.

Second, the therapeutically effective amount of diatrizoate is also not obtainable in the prior art. The new medical use of diatrizoate is markedly different than that for known use. The composition of the present invention claims a unit dosage containing known active ingredient, diatrizoate, in such amount that the unit dosage form is novel and not obvious to have been made up in that amount for the prior art use. The new medical use requires a dose of approximately ten times that for the prior art use, representing a novel, inventive, and allowable claim. Furthermore, the claim to unit dose is clear and specific.

There are several reasons why the invention, a composition, is the ideal pharmaceutical agent for appendicitis diagnosis. First, it represents the only safe and successful diagnostic pharmaceutical, a positive contrast agent, capable of producing an organ-specific positive contrast effect for visualization of the human appendix. More importantly, it has significant advantages over Neutrospect in being administered in a safe and non-invasive means, in addition to having the highest specificity for appendicitis diagnosis currently known or available. The composition of the present invention can be administered in an outpatient setting, whereas Neutrospect can only be administered in the hospitalized setting.

The judicious use of radiation, in conjunction with the CT scan, is also an important reason to use the proposed invention over others used in the prior art. Because the invention is organ-specific and targets the appendix with high specificity, fewer scans of the body are necessary for accurate diagnosis. The appendix is localized with relative ease. In contradistinction to other agents used in the prior art for indirect visualization of the appendix, many CT scan slices are required to visualize the bowel in its entirety, because it cannot be predicted where the appendix, a blind-ending loop, could form an impression or indentation on the distended bowel. The amount of radiation usage could be significant, for example, in patients of pediatric age, or in patients who are immunosuppressed or immunocompromised.

In a preferred embodiment, the composition of the present invention is a fine red powder contained in individually dosed, pyrogen-free, moisture-resistant packet containing 17-grams, sold in cases of 50 packets (for a total of 850 grams/case). The composition preferably includes predetermined amounts of meglumine diatrizonate, sodium diatrizoate, simethicone, famotidine and aspartame. The composition is preferably administered in one dosage that totals 17 grams wherein the weights are as follows: 13.2 grams of meglumine diatrizoate, 2.0 grams of sodium diatrizoate, 40 milligrams of simethicone, 10 milligrams of famotidine and 1.8 grams of aspartame and is dispensed in a liquid, preferably 8 ounces of water. Although the aspartame may be included in the composition of the present invention on its own, as aspartame is also found in various flavored, solid drink mixes and the inclusion of a flavored, solid drink mix allows for easier consumption of the solution by a patient, a predetermined amount of flavored solid drink mix containing aspartame may be substituted or used in addition to aspartame. Although the solid drink mix is preferably raspberry flavored, other flavors may also be used. The composition should be stored at room temperature and protected from light.

The composition is indicated in the clinical evaluation of appendicitis using CT scan of the right lower quadrant, with or without intravenous iodinated contrast media and the product must be prescribed 'as directed' by a licensed physician.

After the composition is mixed with the liquid, the resulting solution is taken orally, optimally within 5 minutes, to achieve a maximum bolus effect. Subsequent CT scans of the appendix are recommended at 50 minutes following oral administration of said composition.

There are no known contraindications to said composition when prescribed as directed. The composition is not indicated for use via the rectal or intravenous routes of administration.

No serious adverse reactions are known to occur with the composition. The composition is not advised in unconscious or obtunded patients, or in patients at risk for aspiration due to impaired swallowing mechanism. The composition is safe and found well-tolerated in the pediatric and elderly population.

There are no known adverse reactions to the composition of the present invention when prescribed as directed by a physician. Minor side effects, including diarrhea, nausea, and abdominal distention, are self-limited and of short duration. There is no known cross reactivity to iodinated intravenous contrast media, consistent with the absence of systemic absorption of organically bound iodine in said composition in the gastrointestinal tract.

The composition can be associated with rare urticaria, or hives (occurring in fewer than 1 in 1000 patients), complete resolution of symptoms is seen following treatment with single-dose diphenhydramine (50 mg IV) and solumedrol (40 mg IV).

Idiosyncratic reactions associated with said composition include all other unspecified reactions that may or may not be dose dependent, but are generally self-limited and of short duration.

Drug reactions or interference with laboratory studies are not known to occur with said composition. Unlike intravenous contrast media, iodine contained in said composition is not systemically absorbed, and poses no risk of renal toxicity or lactic acidosis. Patients taking biguanides do not require cessation for up to 48 hours unless intravenous iodinated contrast agents are administered in conjunction with said composition.

The composition is not known to have either carcinogenic or teratogenic effects in humans.

The composition is not known to cross the placenta or result in systemic absorption, and therefore is not precluded in pregnancy or nursing mothers. However, adequate and well-controlled studies in pregnant women have not been conducted. Because animal reproduction studies are not always predictive of human response, the composition should be used during pregnancy only as deemed medically necessary.

Unpublished clinical data has determined safety and efficacy of said composition in the pediatric population over 2 years of age. Prepared solutions of said composition should be administered at 4 mL per kilogram body weight in the pediatric population.

Fasting is not required prior to administration of said composition. As with all contrast agents, because of the potential for chemical incompatibility, said composition should not be prescribed or mixed with any other solutions or nutritional admixtures.

Regarding general patient advisories regarding the said composition, the following preventative measures should be taken.

1. Patients should inform their physician in the event of pregnancy.
2. Patients should inform their physician in the event of a medical condition that significantly affects the ability to swallow.
3. Patients should not discontinue any prescribed medications unless medically authorized.
4. Patients should inform their physician concerning all medications either prescribed or non-prescription (over-the-counter drugs).
5. Patients should inform their physician regarding any allergies to food or medicinal products, or any immune, autoimmune, or immune deficiency disorders.

EXAMPLE 1

Case Study

A 26-year-old woman presented with vague right lower quadrant pain and tenderness, with equivocal peritoneal signs. A prepared solution of the invention was administered as a single 224-mL oral bolus. Subsequent helical CT scans of the right lower quadrant were performed at 50-min post administration, utilizing 5 mm and 7 mm collimation, 120 kV, 250 mA, and 1.0 s scans, reconstructed in the soft tissue algorithm at a window level of +50 HU and window width of +450. A contrast opacified appendix was demonstrated at 50 minutes, designated as FIG. 1.

EXAMPLE 2

Case Study

Figure 2:
FIG. 2 is a CT scan indicating a classic 'beak sign' of appendicitis after administration of the composition of the present invention.

A 47-year-old man presented with focal right lower quadrant pain, peritoneal tenderness, and fever. A prepared solution of the invention was administered as a single 224-mL oral bolus. Subsequent helical CT scans of the right lower quadrant were performed at 50-min post administration, utilizing 5 mm and 7 mm collimation, 120 kV, 250 mA, and 1.0 s scans, reconstructed in the soft tissue algorithm at a window level of +50 HU and window width of +450. The appendiceal orifice was obstructed, revealing a classic 'beak sign' of appendicitis, with surrounding peritoneal inflammatory inflammatory changes, consistent with appendicitis, designated as FIG. 2.

EXAMPLE 3

Case Study

Figure 3A:
FIGS. 3A and 3B is a CT scan indicating chronic adult appendicitis after administration of the composition of the present invention.
Figure 3B:

A 47-year-old man presented with intermittent right lower quadrant pain on a chronic basis over a period of greater than one month. No clinical signs of appendiceal inflammation were present, including fever, peritoneal tenderness, or leukocytosis. A prepared solution of the invention was administered as a single 224-mL oral bolus. Subsequent helical CT scans of the right lower quadrant were performed at 50-min post administration, utilizing 5 mm and 7 mm collimation, 120 kV, 250 mA, and 1.0 s scans, reconstructed in the soft tissue algorithm at a window level of +50 HU and window width of +450. The appendiceal orifice was obstructed, revealing a thickened appendix and adjacent small calculus, an appendicolith, considered diagnostic for chronic adult appendicitis, designated as FIG. 3.

It has been thus shown that said composition and methods with novel and inventive claims described herein achieve the various objectives of the invention and are well adapted to meet the conditions of practical use.

The invention now having been fully described, it should be understood that it may be embodied in other specific forms or variations without departing from its spirit or essential characteristics. Accordingly, the embodiments described above are to be considered in all respects as illustrative and not restrictive. The scope of the invention being indicated by the appended claims rather than the foregoing description, and all changes which come within the meaning and range of equivalency of the claims to be embraced therein.

The invention claimed is:

1. A method for directly visualizing a human appendix comprising orally administering to a patient a composition comprising a positive contrast agent composition comprising approximately 13.2 grams of meglumine diatrizoate; approximately 2.0 grams of sodium diatrizoate; approximately 40 milligrams of simethicone; approximately 10 milligrams of famotidine; and approximately 1.8 grams of aspartame, and applying computerized tomography to the patient approximately 50 minutes after orally administering the composition to the patient.

2. The method of claim 1 further comprising a step prior to orally administering the composition, said step comprising:
mixing said composition in approximately 8 fluid ounces of liquid.

3. The method of claim 1 wherein:
said approximately 1.8 grams of aspartame is contained in approximately 1.8 grams of solid drink mix.

* * * * *

UNITED STATES PATENT AND TRADEMARK OFFICE
CERTIFICATE OF CORRECTION

PATENT NO.        : 7,378,081 B2                                              Page 1 of 1
APPLICATION NO.   : 11/484296
DATED             : May 27, 2008
INVENTOR(S)       : Giuliano et al.

It is certified that error appears in the above-identified patent and that said Letters Patent is hereby corrected as shown below:

In column 7, line(s) 38-42, delete "uses of ..........of diatrizoate." and insert the same on line 37 after "why" as the continuation of paragraph.

Signed and Sealed this

Twenty-eighth Day of October, 2008

JON W. DUDAS
*Director of the United States Patent and Trademark Office*